US011234659B2

(12) United States Patent
Weed et al.

(10) Patent No.: US 11,234,659 B2
(45) Date of Patent: Feb. 1, 2022

(54) WHEEL AND LIFT UNIT FOR RADIATION IMAGING MODALITIES

(71) Applicant: Analogic Corporation, Peabody, MA (US)

(72) Inventors: Steven Dana Weed, Marblehead, MA (US); Patrick Richard Splinter, Kingston, MA (US); Ronald Elwin Swain, Reading, MA (US)

(73) Assignee: Analogic Corporation, Peabody, MA (US)

( * ) Notice: Subject to any disclaimer, the term of this patent is extended or adjusted under 35 U.S.C. 154(b) by 76 days.

(21) Appl. No.: 16/605,182

(22) PCT Filed: Apr. 14, 2017

(86) PCT No.: PCT/US2017/027645
§ 371 (c)(1),
(2) Date: Oct. 14, 2019

(87) PCT Pub. No.: WO2018/190867
PCT Pub. Date: Oct. 18, 2018

(65) Prior Publication Data
US 2021/0137471 A1 May 13, 2021

(51) Int. Cl.
*A61B 6/00* (2006.01)
*A61B 6/03* (2006.01)
(Continued)

(52) U.S. Cl.
CPC ............ *A61B 6/035* (2013.01); *A61B 6/4452* (2013.01); *A61B 6/4476* (2013.01); *F16C 13/04* (2013.01);
(Continued)

(58) Field of Classification Search
CPC ........ A61B 6/35; A61B 6/4452; A61B 6/4476
See application file for complete search history.

(56) References Cited

U.S. PATENT DOCUMENTS 4,093,862 A * 6/1978 Brandt ................. A61B 6/4447
269/289 MR
2002/0146088 A1 10/2002 Riemer et al.
2012/0241393 A1 9/2012 Roth et al.

FOREIGN PATENT DOCUMENTS

WO 2013/002800 A1 1/2013

OTHER PUBLICATIONS

Written Opinion of the International Searching Authority for PCT Application No. PCT/US2017/027645 dated Mar. 14, 2018, 8 pages.

(Continued)

*Primary Examiner* — Dani Fox
(74) *Attorney, Agent, or Firm* — TraskBritt

(57) ABSTRACT

Among other things, a radiation system is provided. The radiation system includes a stationary unit and a rotating unit that rotates about an axis relative to the stationary unit. A radiation source and a detector array are mounted to the rotating unit. A wheel mechanism at least partially supports the rotating unit and facilitates rotation of the rotating unit relative to the stationary unit. A lift unit is supported by the stationary unit and engages the rotating unit. When the lift unit is in a lowered position, the rotating unit is supported by the wheel mechanism and the lift unit is spaced a distance apart from the rotating unit. When the lift unit is in a raised position, the rotating unit is supported by the lift unit and the rotating unit is spaced a second distance apart from the wheel mechanism.

18 Claims, 12 Drawing Sheets

(51) Int. Cl.
*F16C 13/04* (2006.01)
*F16C 19/50* (2006.01)
(52) U.S. Cl.
CPC ........ *F16C 19/507* (2013.01); *F16C 2300/14* (2013.01); *F16C 2316/10* (2013.01)

(56) References Cited

OTHER PUBLICATIONS

International Search Report for PCT Application No. PCT/US2017/027645 dated Mar. 14, 2018, 7 pages.

* cited by examiner

WHEEL AND LIFT UNIT FOR RADIATION IMAGING MODALITIES

CROSS-REFERENCE TO RELATED APPLICATIONS

This application is a national phase entry under 35 U.S.C. § 371 of International Patent Application PCT/US2017/027645, filed Apr. 14, 2017, designating the United States of America and published as International Patent Publication WO 2018/190867 A1 on Oct. 18, 2018.

TECHNICAL FIELD

The present disclosure relates to a lift unit for supporting a rotating unit for radiation imaging modalities (e.g., imaging modalities that utilize radiation to examine an object), and a wheel unit for imparting rotation to the rotating unit. It finds particular application in the context of computed tomography (CT) scanners. However, the features described herein are not intended to be limited to CT applications and/or other radiation imaging applications.

BACKGROUND

Today, CT and other radiation imaging modalities (e.g., mammography, digital radiography, single-photon emission computed tomography, etc.) are useful to provide information, or images, of interior aspects of an object under examination. Generally, the object is exposed to radiation (e.g., X-rays, gamma rays, etc.), and an image(s) is formed based upon the radiation absorbed and/or attenuated by the interior aspects of the object, or rather an amount of radiation photons that is able to pass through the object. Typically, highly dense aspects of the object (or aspects of the object having a composition comprised of higher atomic number elements) absorb and/or attenuate more radiation than less dense aspects, and thus an aspect having a higher density (and/or high atomic number elements), such as a bone or metal, for example, will be apparent when surrounded by less dense aspects, such as muscle or clothing.

Radiation imaging modalities generally comprise, among other things, one or more radiation sources (e.g., an X-ray source, Gamma-ray source, etc.) and a detector array comprised of a plurality of pixels or detector cells that are respectively configured to convert radiation that has traversed the object into signals that may be processed to produce the image(s). As an object is passed between the radiation source(s) and the detector array, radiation is absorbed/attenuated by the object, causing changes in the amount/energy of detected radiation. Using information derived from the detected radiation, radiation imaging modalities are configured to generate images that can be used to detect items within the object that may be of particular interest (e.g., body characteristics, threat items, etc.). These images may be two-dimensional images or three-dimensional images.

To generate three-dimensional images, at least one of the radiation source(s) or the detector array are rotated relative to the object under examination to acquire information about the object from various views. In CT scanners, the radiation source(s) and the detector array are typically mounted to a rotating unit (e.g., a disk or drum) that is rotated about the object under examination. The rotating unit must be sized to accommodate the object (e.g., luggage, a human patient, etc.) in a center bore, and thus the outer diameter of such disks or drums may exceed five feet.

Rotation of the rotating unit may be imparted by a wheel unit, such as one or more bearings that are typically sized to match the diameter of the disk or drum and a belt drive system that physically rotates the rotating unit. The rotating unit can be supported by and rotated relative to the wheel unit, or the belt drive system thereof. At times, it may be necessary to perform an inspection and/or maintenance on the wheel unit. Due to the size of these CT systems, manufacturing and/or replacing a bearing can be difficult and costly. Moreover, replacing the bearing can be time consuming, thus reducing the amount of time that the CT system is in service.

BRIEF SUMMARY

Aspects of the present disclosure address the above matters, and others. According to one aspect a wheel unit for a radiation system is provided. The wheel unit comprises a wheel mechanism configured to at least partially support a rotating unit and facilitate rotation of the rotating unit relative to a stationary unit. The wheel mechanism comprises at least one roller that is configured to impart rotation to the rotating unit. A radiation source and a detector array are mounted to the rotating unit. A support structure is configured to support the wheel mechanism. The support structure defines an opening that is sized to receive the wheel mechanism. An attachment structure is configured to attach the wheel mechanism to the support structure. When the attachment structure is in a locked position, the attachment structure engages the wheel mechanism and the support structure such that the wheel mechanism is attached to the support structure. When the attachment structure is in an unlocked position, the attachment structure does not engage at least one of the wheel mechanism or the support structure such that the wheel mechanism is detached from the support structure and removable from the support structure through the opening.

According to another aspect, a radiation system comprises a stationary unit and a rotating unit configured for rotation about an axis relative to the stationary unit. The axis lies within a plane that bisects the rotating unit. The rotating unit comprises a first rotational surface extending about the axis and a second rotational surface extending about the axis. A radiation source and a detector array are mounted to the rotating unit. A wheel mechanism set is configured to at least partially support the rotating unit at the first rotational surface and facilitate rotation of the rotating unit relative to the stationary unit. The wheel mechanism set comprises a wheel mechanism configured to rotationally support the rotating unit at a first location of the first rotational surface. The first location lies on a first side of the plane. A second wheel mechanism is configured to rotationally support the rotating unit at a second location of the first rotational surface. The second location lies on the first side of the plane. A second wheel mechanism set is configured to at least partially support the rotating unit at the second rotational surface and facilitate rotation of the rotating unit relative to the stationary unit. The second wheel mechanism set comprises a third wheel mechanism configured to rotationally support the rotating unit at a third location of the second rotational surface. The third location lies on the first side of the plane. A fourth wheel mechanism is configured to rotationally support the rotating unit at a fourth location of the second rotational surface. The fourth location lies on the first side of the plane.

According to another aspect, a radiation system comprises a stationary unit and a rotating unit configured for rotation about an axis relative to the stationary unit. A radiation source and a detector array are mounted to the rotating unit. A wheel mechanism is configured to at least partially support the rotating unit and facilitate rotation of the rotating unit relative to the stationary unit. A lift unit is supported by the stationary unit and configured to engage the rotating unit. When the lift unit is in a lowered position relative to the rotating unit, the rotating unit is supported by the wheel mechanism and the lift unit is spaced a distance apart from the rotating unit. When the lift unit is in a raised position relative to the rotating unit, the rotating unit is supported by the lift unit and the rotating unit is spaced a second distance apart from the wheel mechanism.

Those of ordinary skill in the art will appreciate still other aspects of the present disclosure upon reading and understanding the appended description.

BRIEF DESCRIPTION OF THE DRAWINGS

This disclosure is illustrated by way of example and not limitation in the figures of the accompanying drawings, wherein like references generally indicate similar elements and wherein.

DETAILED DESCRIPTION

Figure 1:
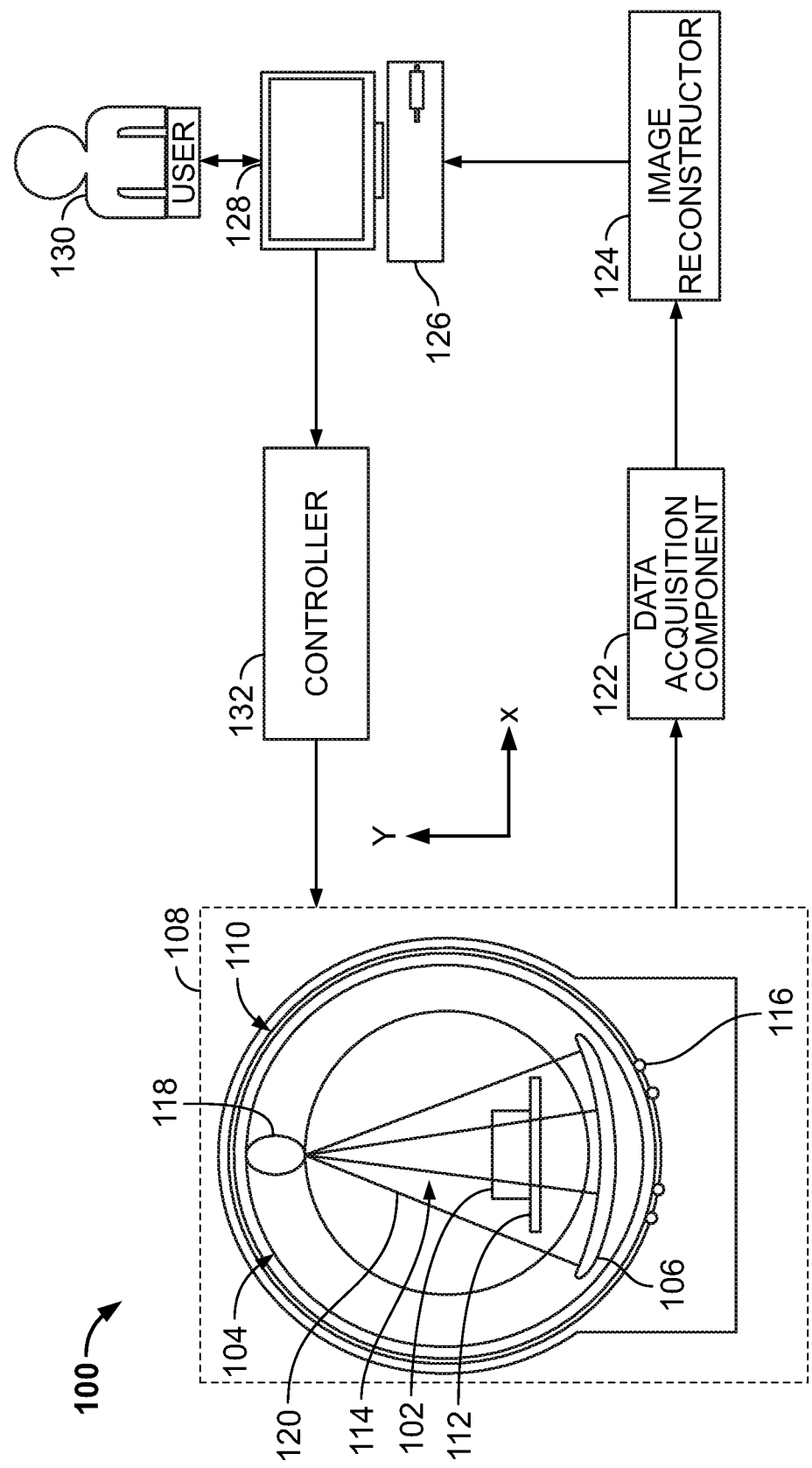
FIG. 1 illustrates an example environment of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a wheel unit for a radiation system. The wheel unit comprises a wheel mechanism that can at least partially support a rotating unit and facilitate rotation of the rotating unit relative to a stationary unit. The wheel mechanism can be supported by a support structure that is attached to the stationary unit. The support structure defines an opening that is sized to receive the wheel mechanism. An attachment structure can attach the wheel mechanism to the support structure. When the attachment structure is in a locked position, the wheel mechanism is attached to the support structure. When the attachment structure is in an unlocked position, the wheel mechanism is removable from the support structure through the opening. In this way, access to the wheel mechanism (e.g., for maintenance, inspection, etc.) is facilitated. That is, through the removal of the attachment structure, the wheel mechanism can be detached from the support structure. Conversely, the wheel mechanism can also be attached to the support structure by the attachment structure.

When the wheel mechanism is to be detached from the support structure, the rotating unit can be supported by a lift unit. The lift unit is supported by the stationary unit and is configured to selectively engage the rotating unit. For example, when the lift unit is in a lowered position relative to the rotating unit, the rotating unit is supported by the wheel mechanism. When the lift unit is in a raised position, relative to the rotating unit, the rotating unit is supported by the lift unit. As such, when the rotating unit is supported by the lift unit, the rotating unit is lifted off of the wheel mechanism to enable the wheel mechanism to be removed for maintenance, inspection, etc.

FIG. 1 is an illustration of an example environment 100 comprising an example radiation imaging modality (e.g., radiation system) that may be configured to generate data (e.g., images) representative of an object 102 or aspect(s) thereof under examination. It will be appreciated that the features described herein may find applicability to other imaging modalities besides the example computed tomography (CT) scanner illustrated in FIG. 1. For example, the rotating unit 104 described herein may find applicability to other types of radiation imaging modalities, such SPECT scanners. Moreover, the arrangement of components and/or the types of components included in the example environment 100 are for illustrative purposes only. For example, the rotating unit 104 (e.g., a rotating gantry) may comprise additional components to support the operation of a radiation source 118 and/or detector array 106, such as a cooling unit, power units, etc. As another example, at least a portion of a data acquisition component 122 may be comprised within and/or attached to the detector array 106.

In the example environment 100, an examination unit 108 of the imaging modality is configured to examine one or more objects 102. The examination unit 108 can comprise a rotating unit 104 and a stationary unit 110, also referred to herein as a frame, which may encase and/or surround as least a portion of the rotating unit 104 (e.g., as illustrated with an outer, stationary ring, surrounding an outside edge of an inner, rotating ring). During an examination of the object(s) 102, the object(s) 102 can be placed on an object support 112, such as a bed or conveyor belt, for example, that is selectively positioned in an examination region 114 (e.g., a hollow bore in the rotating unit 104), and the rotating unit 104 can be rotated and/or supported about the object(s) 102 by a rotator 116, such as a bearing, motor, belt wheel unit, drive shaft, chain, roller truck, etc.

The rotating unit 104 may surround a portion of the examination region 114 and may comprise one or more radiation sources 118 (e.g., an ionizing X-ray source, gamma radiation source, etc.) and a detector array 106 that is mounted on a substantially diametrically opposite side of the rotating unit 104 relative to the radiation source(s) 118.

During an examination of the object(s) 102, the radiation source(s) 118 emits fan or cone shaped radiation 120 configurations from a focal spot(s) of the radiation source(s) 118 (e.g., a region within the radiation source(s) 118 from which radiation 120 emanates) into the examination region 114. It will be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear (e.g., one-dimensional) or two-dimensional array of elements (sometimes referred to as pixels, channels, or detector cells) disposed as a single row or multiple rows in the shape of spherical arc, typically having a center of curvature at the focal spot of the radiation source(s) 118, for example. As the rotating unit 104 rotates, the detector array 106 is configured to directly convert (e.g., using amorphous selenium and/or other direct conversion materials) and/or indirectly convert (e.g., using Cesium Iodide (CsI) and/or other indirect conversion materials) detected radiation into electrical signals.

Signals that are produced by the detector array 106 may be transmitted to a data acquisition component 122 that is in operable communication with the detector array 106. Typically, the data acquisition component 122 is configured to convert the electrical signals output by the detector array 106 into digital data and/or to combine the digital data acquired during a measuring interval. The collection of digital output signals for a measuring interval may be referred to as a "projection" or a "view."

The example environment 100 also illustrates an image reconstructor 124 that is operably coupled to the data acquisition component 122 and is configured to generate one or more images representative of the object 102 under examination based at least in part upon signals output from the data acquisition component 122 using suitable analytical, iterative, and/or other reconstruction technique (e.g., tomosynthesis reconstruction, back-projection, iterative reconstruction, etc.).

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input that can direct operations of the object examination unit 108 (e.g., a speed of rotation for the rotating unit 104, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

It will be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components to perform additional features, functions, etc. (e.g., such as automatic threat detection).

Figure 2:
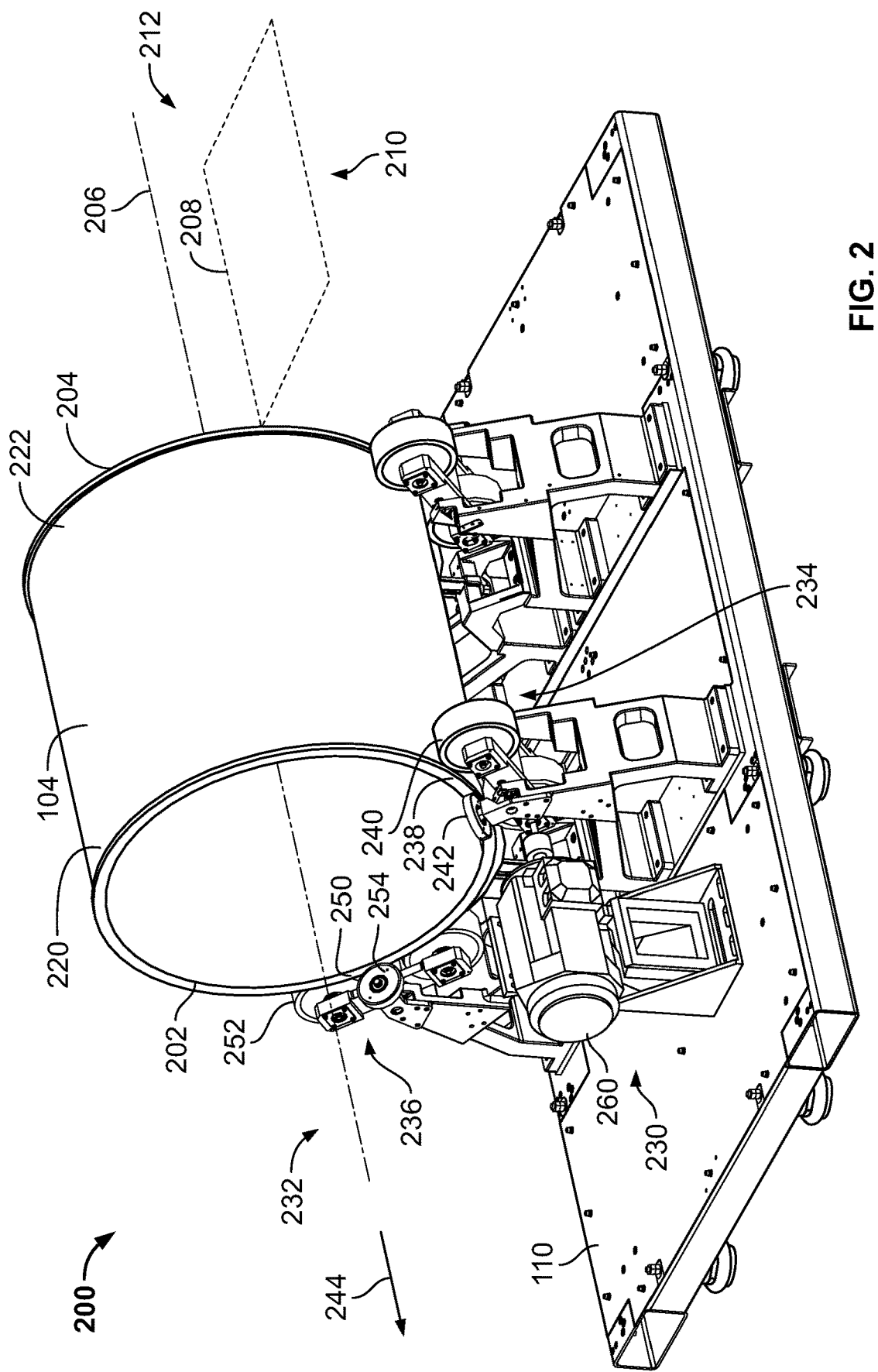
FIG. 2 illustrates an example radiation system having a stationary unit and a rotating unit.

FIG. 2 illustrates an example radiation system 200 (e.g., examination unit 108) that can be used within the example environment 100 of FIG. 1. In an example, the radiation system 200 comprises the rotating unit 104 and the stationary unit 110. The rotating unit 104 can extend between a first end 202 and a second end 204 along an axis 206. In an example, with the radiation source 118 and the detector array 106 mounted to the rotating unit 104, the rotating unit 104 is configured to rotate about the axis 206 relative to the stationary unit 110.

The axis 206 may lie within a plane 208 that bisects the rotating unit 104. In an example, the plane 208 can extend substantially parallel to the stationary unit 110 and/or to a surface upon which the radiation system 200 rests. In this way, the plane 208 can define a first side 210 and a second side 212, wherein the first side 210 comprises a bottom portion (e.g., a bottom half) of the rotating unit 104 while the second side 212 comprises a top portion (e.g., a top half) of the rotating unit 104.

The rotating unit 104 can comprise one or more rotational surfaces, such as a first rotational surface 220 extending about the axis 206 and a second rotational surface 222 extending about the axis 206. In an example, the first rotational surface 220 and the second rotational surface 222 can be defined at an outer radial side of the rotating unit 104. The first rotational surface 220 and the second rotational surface 222 can extend substantially circularly (e.g., by having a circular shape) about the axis 206. In an example, the first rotational surface 220 may be disposed adjacent to the first end 202 of the rotating unit 104, while the second rotational surface 222 may be disposed adjacent to the second end 204 of the rotating unit 104. The first rotational surface 220 and the second rotational surface 222 can define a substantially smooth outer surface about the axis 206.

The radiation system 200 comprises a wheel unit 230 for supporting and/or facilitating rotation of the rotating unit 104. In an example, the wheel unit 230 comprises a wheel mechanism set 232. The wheel mechanism set 232 is configured to at least partially support the rotating unit 104 at the first rotational surface 220 and facilitate rotation of the rotating unit 104 relative to the stationary unit 110. In an example, the wheel mechanism set 232 can be supported by and/or attached to the stationary unit 110. The wheel mechanism set 232 can be positioned adjacent to the first end 202 of the rotating unit 104.

The wheel mechanism set 232 comprises a wheel mechanism 234 and a second wheel mechanism 236. The wheel mechanism 234 is configured to at least partially support the rotating unit 104 and facilitate rotation of the rotating unit 104 relative to the stationary unit 110. In an example, the wheel mechanism 234 can rotationally support the rotating unit 104 at a first location 238 of the first rotational surface 220, with the first location 238 lying on the first side 210 of the plane 208. In this way, the wheel mechanism 234 can contact the bottom portion of the rotating unit 104 (e.g., an axial face), with the rotating unit 104 resting upon the wheel mechanism 234 due to the force of gravity.

In an example, the wheel mechanism 234 comprises at least one roller 240 that is configured to support and/or impart the rotation to the rotating unit 104 about the axis 206. The wheel mechanism 234 may comprise an axial roller 242 that is oriented substantially perpendicular to the at least one roller 240. The axial roller 242 can contact and/or engage the first end 202 (e.g., a radial face) of the rotating unit 104. In this way, the axial roller 242 can limit movement of the rotating unit 104 along the axis 206. For example, the axial roller 242 can limit unintended movement of the rotating unit 104 along a first direction 244 that is substantially parallel to the axis 206.

The second wheel mechanism 236 is configured to at least partially support the rotating unit 104 and facilitate rotation of the rotating unit 104 relative to the stationary unit 110. In an example, the second wheel mechanism 236 can rotationally support the rotating unit 104 at a second location 250 of the first rotational surface 220, with the second location 250 lying on the first side 210 of the plane 208. In this way, the second wheel mechanism 236 can contact the bottom portion of the rotating unit 104, with the rotating unit 104 resting upon the second wheel mechanism 236 due to the force of gravity.

The second wheel mechanism 236 can be spaced apart from the wheel mechanism 234 along the first rotational surface 220. In an example, the wheel mechanism 234 and the second wheel mechanism 236 can be spaced apart between about 60 degrees to about 120 degrees, or, in an example, between about 80 degrees to about 100 degrees. In this way, the rotating unit 104 can be in contact with and supported by the wheel mechanism 234 and the second wheel mechanism 236 at the first rotational surface 220.

In an example, the second wheel mechanism 236 comprises at least one second roller 252 that is configured to support and/or impart the rotation to the rotating unit 104 about the axis 206. The second wheel mechanism 236 may comprise a second axial roller 254 that is oriented substantially perpendicular to the at least one second roller 252. The second axial roller 254 can contact and/or engage the first end 202 of the rotating unit 104. In this way, the second axial roller 254 can limit movement of the rotating unit 104 along the axis 206. For example, the second axial roller 254 can limit unintended movement of the rotating unit 104 along the first direction 244 that is substantially parallel to the axis 206.

In an example, the wheel unit 230 comprises a motor 260 that can cause rotation of the rotating unit 104. For example, the motor 260 may be coupled to one of the rollers 240 of the wheel mechanism 234. In an example, a shaft can be attached to the motor 260 and the roller 240, such that the motor 260 can cause the shaft to rotate, which may thus cause the roller 240 to rotate. This rotation may be imparted to the rotating unit 104, whereupon the rotating unit 104 can rotate. In this way, the motor 260 can impart rotation to the roller 240 thus causing the rotating unit 104 to rotate.

It will be appreciated that the wheel unit 230 is not limited to being coupled to the motor 260. Rather, in an example, rotation of the rotating unit 104 can be imparted in other ways. For example, rotation may be imparted to the rotating unit 104 by another type of drive mechanism, such as a belt, chain, etc., with the belt, chain, etc., engaging the rotating unit 104 and causing rotation of the rotating unit 104. In this way, the wheel unit 230 (e.g., comprising the wheel mechanism set 232 and a second wheel mechanism set 300 illustrated in FIG. 3) may support the rotating unit 104 while not imparting rotating to the rotating unit 104. Rather, the wheel unit 230 can facilitate rotation of the rotating unit 104 relative to the wheel unit 230, while a belt, a chain, etc., can engage the rotating unit 104 and cause the rotating unit 104 to rotate.

Figure 3:
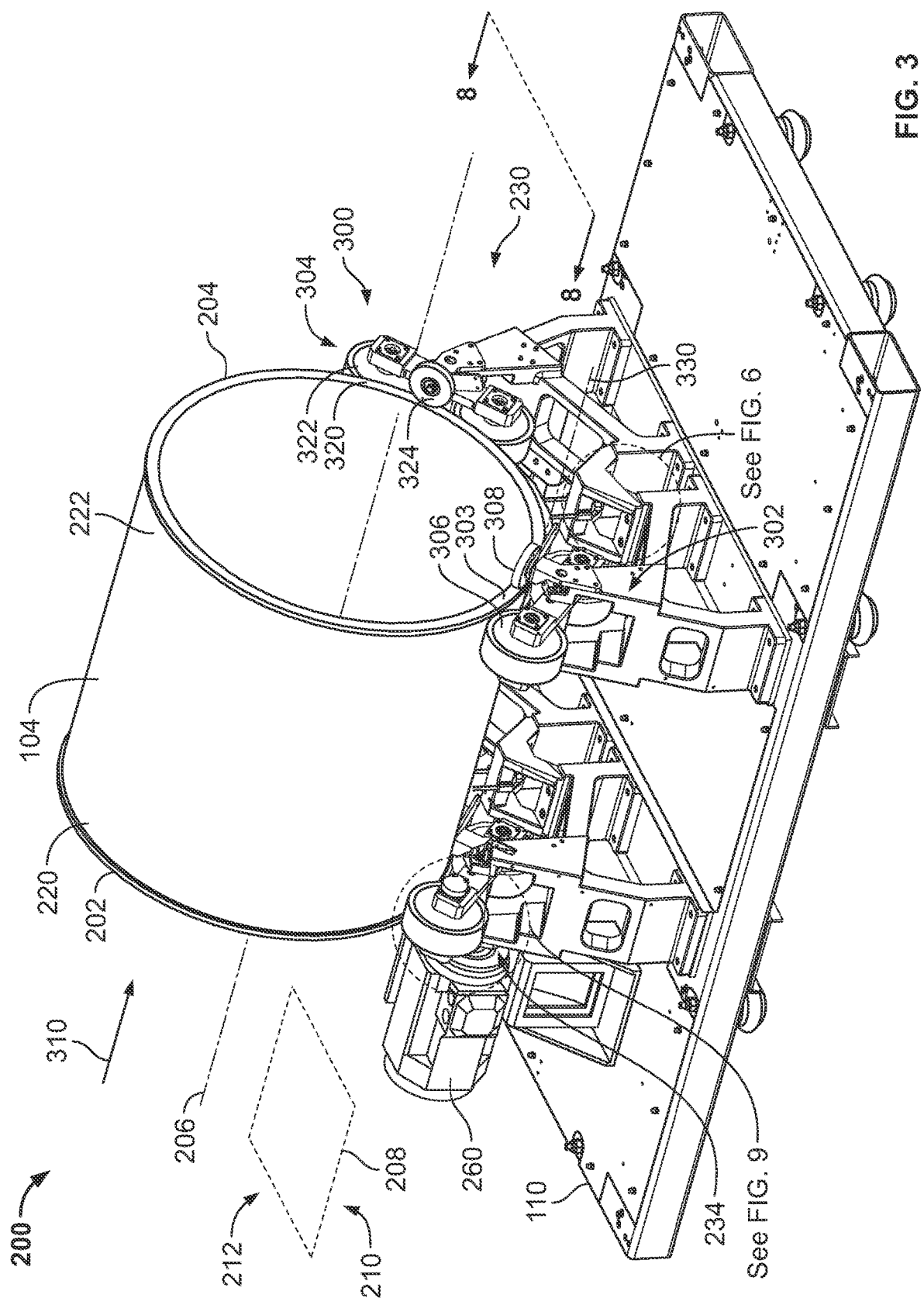
FIG. 3 illustrates an example radiation system having a stationary unit and a rotating unit.

Referring to FIG. 3, the second end 204 of the rotating unit 104 is illustrated. In an example, the wheel unit 230 comprises a second wheel mechanism set 300. The second wheel mechanism set 300 is configured to at least partially support the rotating unit 104 at the second rotational surface 222 and facilitate rotation of the rotating unit 104 relative to the stationary unit 110. In an example, the second wheel mechanism set 300 can be supported by and/or attached to the stationary unit 110. The second wheel mechanism set 300 can be positioned adjacent to the second end 204 of the rotating unit 104.

The second wheel mechanism set 300 comprises a third wheel mechanism 302 and a fourth wheel mechanism 304. The third wheel mechanism 302 is configured to at least partially support the rotating unit 104 and facilitate rotation of the rotating unit 104 relative to the stationary unit 110. In an example, the third wheel mechanism 302 can rotationally support the rotating unit 104 at a third location 303 of the second rotational surface 222, with the third location 303 lying on the first side 210 of the plane 208. In this way, the third wheel mechanism 302 can contact the bottom portion of the rotating unit 104, with the rotating unit 104 resting upon the third wheel mechanism 302 due to the force of gravity.

In an example, the third wheel mechanism 302 comprises at least one third roller 306 that is configured to support and/or impart the rotation to the rotating unit 104 about the axis 206. The third wheel mechanism 302 may comprise a third axial roller 308 that is oriented substantially perpendicular to the at least one third roller 306. The third axial roller 308 can contact and/or engage the second end 204 of the rotating unit 104. In this way, the third axial roller 308 can limit movement of the rotating unit 104 along the axis 206. For example, the third axial roller 308 can limit unintended movement of the rotating unit 104 along a second direction 310 that is substantially parallel to the axis 206. In an example, the rotating unit 104 may be disposed between the axial roller 242 and the third axial roller 308. As such, the axial roller 242 and the third axial roller 308 can limit unintended movement of the rotating unit 104 in the first direction 244 or the second direction 310 along the axis 206.

The fourth wheel mechanism 304 is configured to at least partially support the rotating unit 104 and facilitate rotation of the rotating unit 104 relative to the stationary unit 110. In an example, the fourth wheel mechanism 304 can rotationally support the rotating unit 104 at a fourth location 320 of the second rotational surface 222, with the fourth location 320 lying on the first side 210 of the plane 208. In this way, the fourth wheel mechanism 304 can contact the bottom portion of the rotating unit 104, with the rotating unit 104 resting upon the fourth wheel mechanism 304 due to the force of gravity.

The fourth wheel mechanism 304 can be spaced apart from the third wheel mechanism 302 along the second rotational surface 222. In an example, the third wheel mechanism 302 and the fourth wheel mechanism 304 can be spaced apart between about 60 degrees to about 120 degrees, or, in an example, between about 80 degrees to about 100 degrees. In this way, the rotating unit 104 can be in contact with and supported by the third wheel mechanism 302 and the fourth wheel mechanism 304 at the second rotational surface 222.

In an example, the fourth wheel mechanism 304 comprises at least one fourth roller 322 that is configured to support and/or impart the rotation to the rotating unit 104 about the axis 206. The fourth wheel mechanism 304 may comprise a fourth axial roller 324 that is oriented substantially perpendicular to the at least one fourth roller 322. The fourth axial roller 324 can contact and/or engage the second end 204 of the rotating unit 104. In this way, the fourth axial roller 324 can limit movement of the rotating unit 104 along the axis 206. For example, the fourth axial roller 324 can limit unintended movement of the rotating unit 104 along the second direction 310 that is substantially parallel to the axis 206. In an example, the rotating unit 104 may be disposed between the second axial roller 254 and the fourth axial roller 324. As such, the second axial roller 254 and the fourth axial roller 324 can limit unintended movement of the rotating unit 104 in the first direction 244 or the second direction 310 along the axis 206.

In an example, the first location 238 of the wheel mechanism 234 along the first rotational surface 220 can substantially match the third location 303 of the third wheel mechanism 302 along the second rotational surface 222. For example, a wheel axis 330 can intersect the wheel mechanism 234 and the third wheel mechanism 302, with the wheel axis 330 extending substantially parallel to the axis 206. Likewise, in an example, the second location 250 of the second wheel mechanism 236 along the first rotational surface 220 can substantially match the fourth location 320 of the fourth wheel mechanism 304 along the second rotational surface 222. In this way, the rotating unit 104 can be supported at a plurality of locations (e.g., four total locations in the examples of FIGS. 2 and 3) at both the first end 202 and the second end 204.

Figure 4:
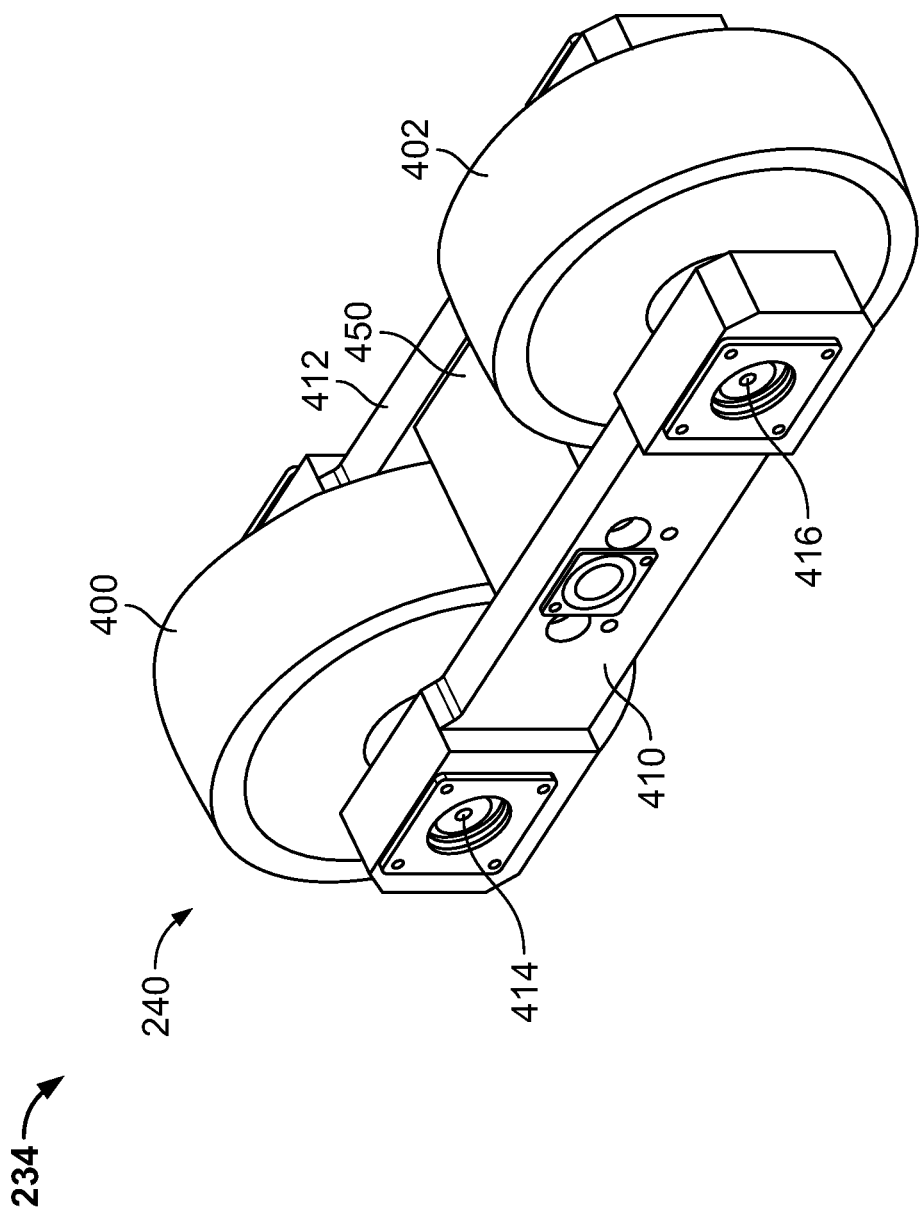
FIG. 4 illustrates an example wheel mechanism for supporting and imparting rotation to the rotating unit.
Figure 5:
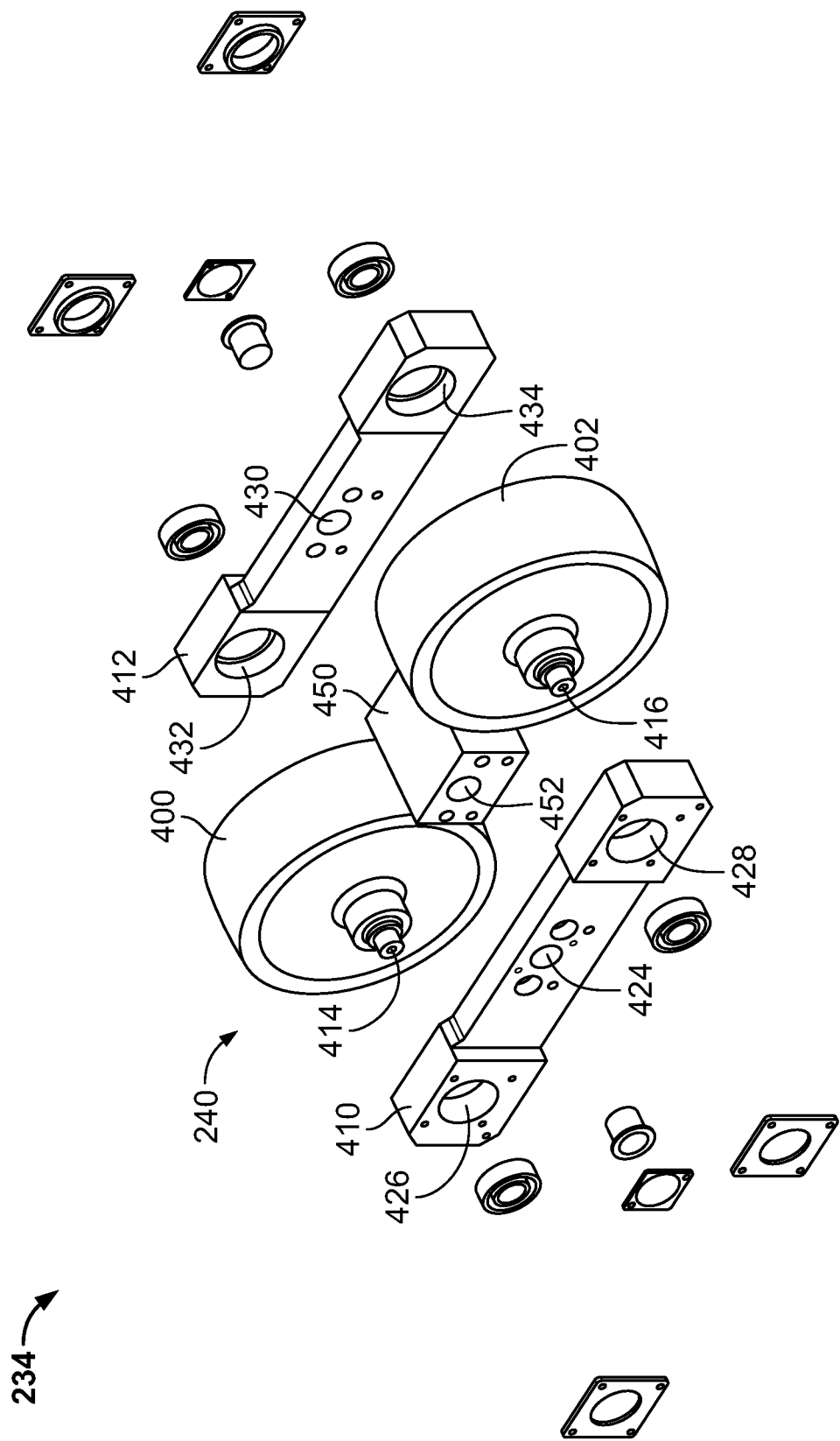
FIG. 5 illustrates an example wheel mechanism for supporting and imparting rotation to the rotating unit.

Referring to FIGS. 4 and 5, an example of the wheel mechanism 234 is illustrated. FIG. 4 illustrates the wheel mechanism 234 in an assembled and/or operational state, while FIG. 5 illustrates a partially exploded illustration of the wheel mechanism 234. It will be appreciated that the second wheel mechanism 236, the third wheel mechanism 302, and/or the fourth wheel mechanism 304 may be substantially similar or identical in structure, configuration, construction, etc., to the wheel mechanism 234 illustrated in FIGS. 4 and 5.

The wheel mechanism 234 can comprise the at least one roller 240, such as a first roller 400 and a second roller 402. The first roller 400 and the second roller 402 may be arranged end to end, so as to extend substantially parallel to and co-planar with respect to each other. The first roller 400 and the second roller 402 are configured to contact the first rotational surface 220 of the rotating unit 104. In an example, the first roller 400 and the second roller 402 may comprise a resilient metal or non-metal material, such as nylon, rubber, other polymers, etc. The material selected for the first roller 400 and the second roller 402 can function to dampen mechanical noise and limit compression of the first roller 400 and the second roller 402. In an example, the material may accommodate for thermal expansion of the rotating unit 104. In this way, the first roller 400 and the second roller 402 are configured to impart rotation to the rotating unit 104. For example, the motor 260 may be coupled to the first roller 400, with the motor 260 imparting rotation to the first roller 400.

The wheel mechanism 234 comprises one or more linking structures for attaching the first roller 400 and the second roller 402. For example, the wheel mechanism 234 comprises a first linking structure 410 and a second linking structure 412. The first linking structure 410 and the second linking structure 412 can extend substantially parallel to and spaced apart from each other. The first roller 400 and the second roller 402 can be disposed in a space defined between the first linking structure 410 and the second linking structure 412. In an example, the first roller 400 comprises a first axle 414 that extends through a center of the first roller 400, while the second roller 402 comprises a second axle 416 that extends through a center of the second roller 402.

In an example, the first linking structure 410 can be attached to the first axle 414 of the first roller 400 at a first end, and to the second axle 416 of the second roller 402 at a second end. Likewise, in an example, the second linking structure 412 can be attached to the first axle 414 of the first roller 400, and to the second axle 416 of the second roller 402 at a second end.

The first linking structure 410 comprises one or more openings (e.g., illustrated in FIG. 5). For example, the first linking structure 410 may comprise a linking opening 424, a first roller opening 426, and a second roller opening 428. The first roller opening 426 may be sized to receive a portion of the first axle 414 of the first roller 400 and/or one or more attachment structures for attaching the first axle 414 to the first linking structure 410. The second roller opening 428 may be sized to receive a portion of the second axle 416 of the second roller 402 and/or one or more attachment structures for attaching the second axle 416 to the first linking structure 410.

The second linking structure 412 comprises one or more openings. For example, the second linking structure 412 may comprise a second linking opening 430, a third roller opening 432, and a fourth roller opening 434. The third roller opening 432 may be sized to receive a portion of the first axle 414 of the first roller 400 and/or one or more attachment structures for attaching the first axle 414 to the second linking structure 412. The fourth roller opening 434 may be sized to receive a portion of the second axle 416 of the second roller 402 and/or one or more attachment structures for attaching the second axle 416 to the second linking structure 412.

The wheel mechanism 234 comprises a third linking structure 450 that is configured to attach the first linking structure 410 and the second linking structure 412. For example, the third linking structure 450 can be disposed between the first roller 400 and the second roller 402. The third linking structure 450 can further be disposed between the first roller 400 and the second roller 402. The third linking structure 450 defines a third linking opening 452 that can be aligned with the linking opening 424 of the first linking structure 410 and the second linking opening 430 of the second linking structure 412. In this way, an attachment structure is configured to be received through the linking opening 424 of the first linking structure 410, the second linking opening 430 of the second linking structure 412, and the third linking opening 452 of the third linking structure 450.

Figure 6:
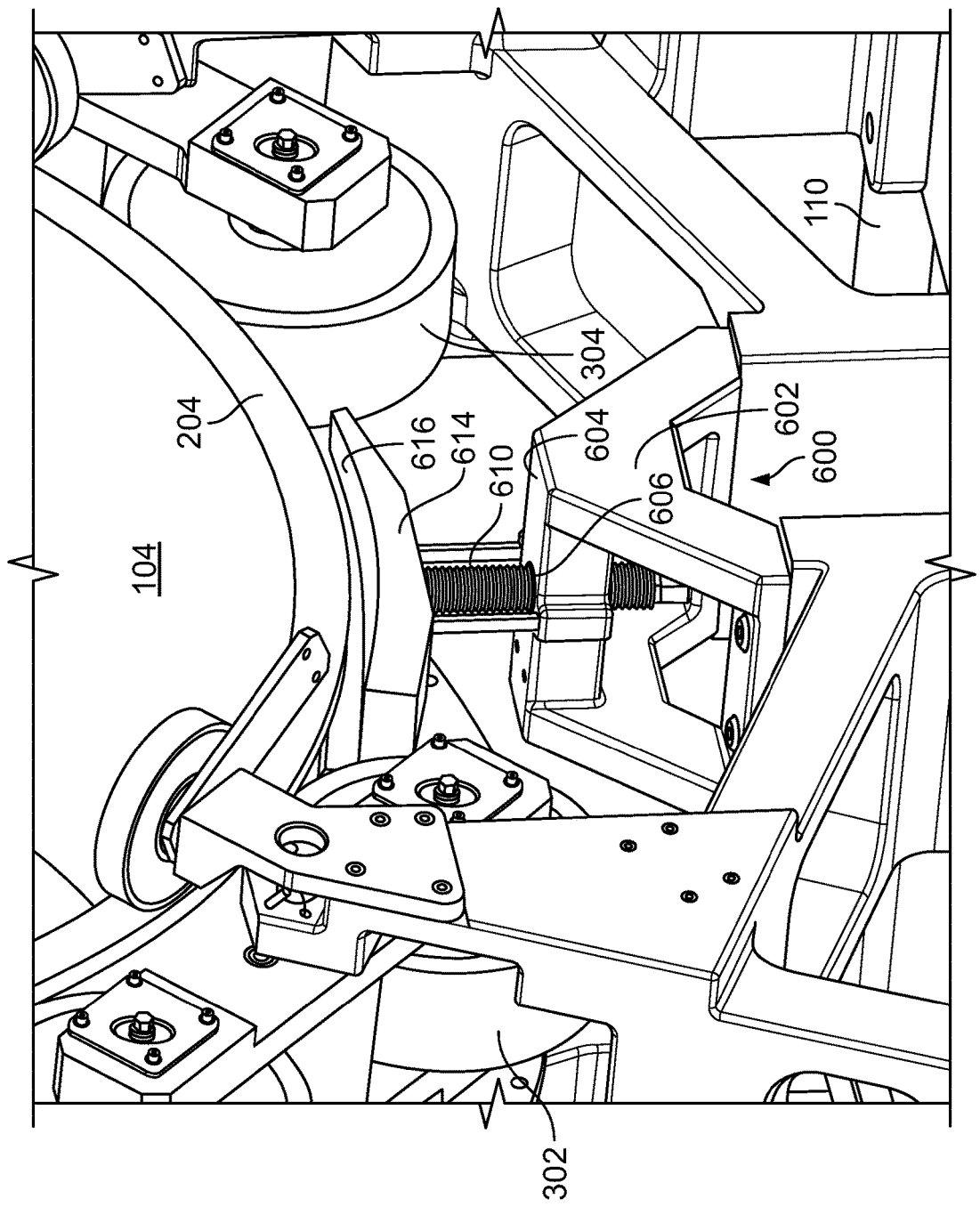
FIG. 6 illustrates an example lift unit in a lowered position.

Referring to FIG. 6, a lift unit 600 for lifting the rotating unit 104 between a lowered position and a raised position is illustrated. In an example, the lift unit 600 may be supported by the stationary unit 110 and is configured to engage the rotating unit 104, with the lift unit 600 extending substantially perpendicular to the axis 206. The lift unit 600 is illustrated as being positioned at the second end 204 of the rotating unit 104 between the third wheel mechanism 302 and the fourth wheel mechanism 304. A second lift unit may be positioned at the first end 202 of the rotating unit 104 between the wheel mechanism 234 and the second wheel mechanism 236.

The lift unit 600 can be attached to the stationary unit 110 by a base 602. In an example, the base 602 can be attached to the stationary unit 110. In an example, the base 602 comprises a base wall 604 that defines a base opening 606. The base opening 606 is configured to receive a portion of the lift unit 600, with the lift unit 600 being movable relative to the base 602.

The lift unit 600 comprises a lift shaft 610 that can engage the base 602. For example, the lift shaft 610 can be received within the base opening 606 of the base 602. In an example, the lift shaft 610 comprises a threaded shaft, such as a male threading. The base wall 604 defining the base opening 606 can likewise comprise a threading, such as female threading. In this way, when the lift shaft 610 is received within the base opening 606, the male threading of the lift shaft 610 can engage and mate with the female threading of the base opening 606. Such an engagement allows for the lift shaft 610 to be moved and/or adjusted relative to the base 602. In an example, a position (e.g., height) of the lift shaft 610 can be adjusted with respect to the base 602 by rotating the lift shaft 610 relative to the base 602.

The lift unit 600 comprises an engagement member 614. The engagement member 614 can be attached to an end of the lift shaft 610, with the engagement member 614 located between the rotating unit 104 and the base 602. In an example, movement of the lift shaft 610 can cause corresponding movement of the engagement member 614. The engagement member 614 comprises an engagement surface 616 that is configured to contact the rotating unit 104 when the lift unit 600 is in a raised position. In an example, the engagement member 614 can have a shape that substantially matches a shape of an outer surface of the rotating unit 104. For example, the outer surface (e.g., an axial surface) of the rotating unit 104 can have a substantially circular or cylindrical shape. In such an example, the engagement surface 616 of the engagement member 614 can likewise have a rounded, non-linear shape that is configured to match the outer surface of the rotating unit 104. In this way, when the engagement member 614 contacts the rotating unit 104, the engagement member 614 can receive the rotating unit 104 and limit the rotating unit 104 from inadvertently disengaging from the engagement member 614.

The lift unit 600 illustrated in FIG. 6 is in a lowered position relative to the rotating unit 104. That is, in the lowered position, the rotating unit 104 may be supported by the wheel unit 230 (e.g., the wheel mechanism 234, the second wheel mechanism 236, the third wheel mechanism 302, and the fourth wheel mechanism 304). The lift unit 600 may therefore be spaced a distance apart from the rotating unit 104, such that a gap, a space, an opening, etc., may be defined between the engagement surface 616 of the engagement member 614 and the rotating unit 104. As such, in an example, when the lift unit 600 is in the lowered position, the rotating unit 104 can be supported by the wheel unit 230, whereupon the wheel unit 230 may facilitate rotation of the rotating unit 104 relative to the stationary unit 110.

Figure 7:
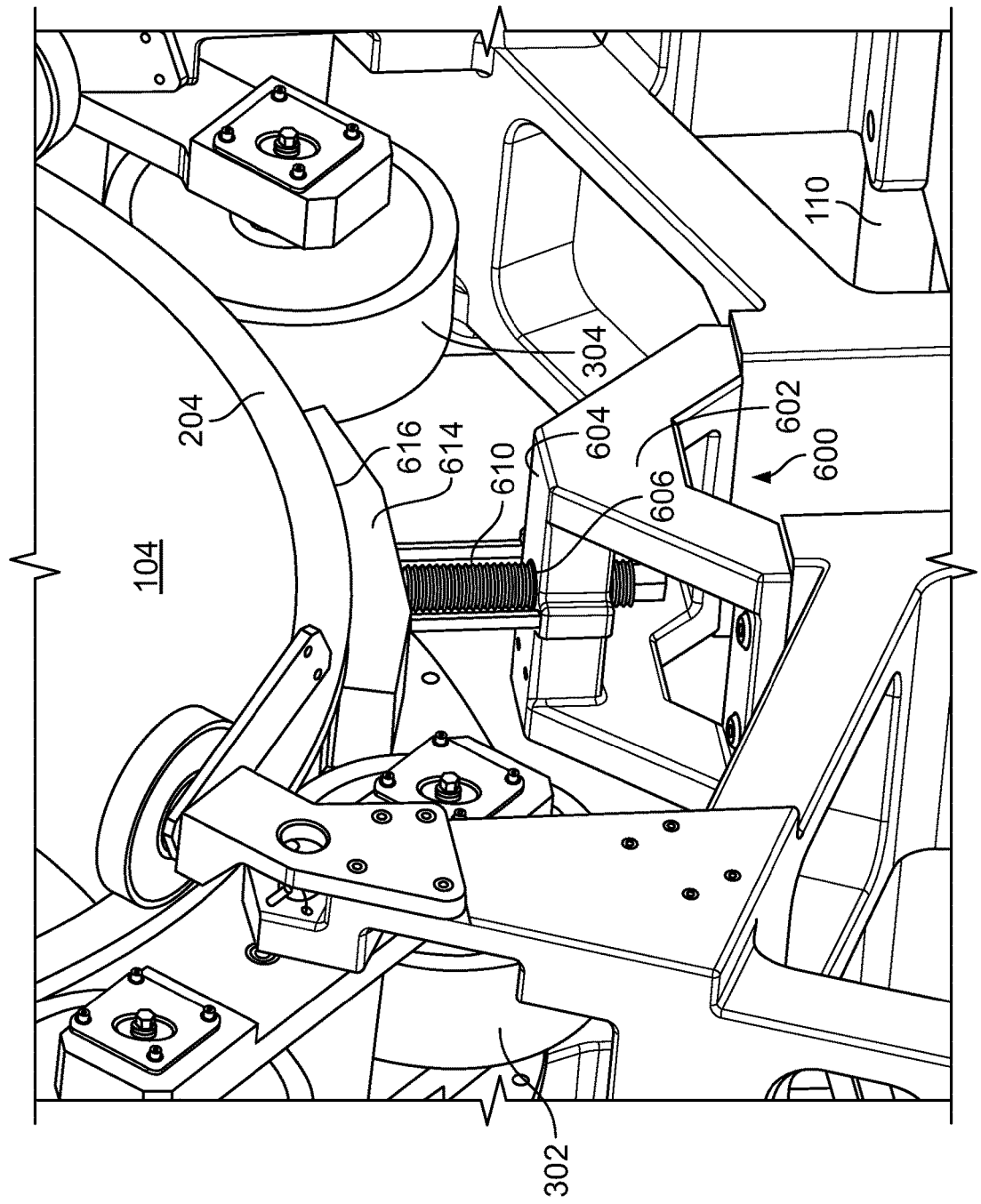
FIG. 7 illustrates an example lift unit in an intermediate position.
Figure 8:
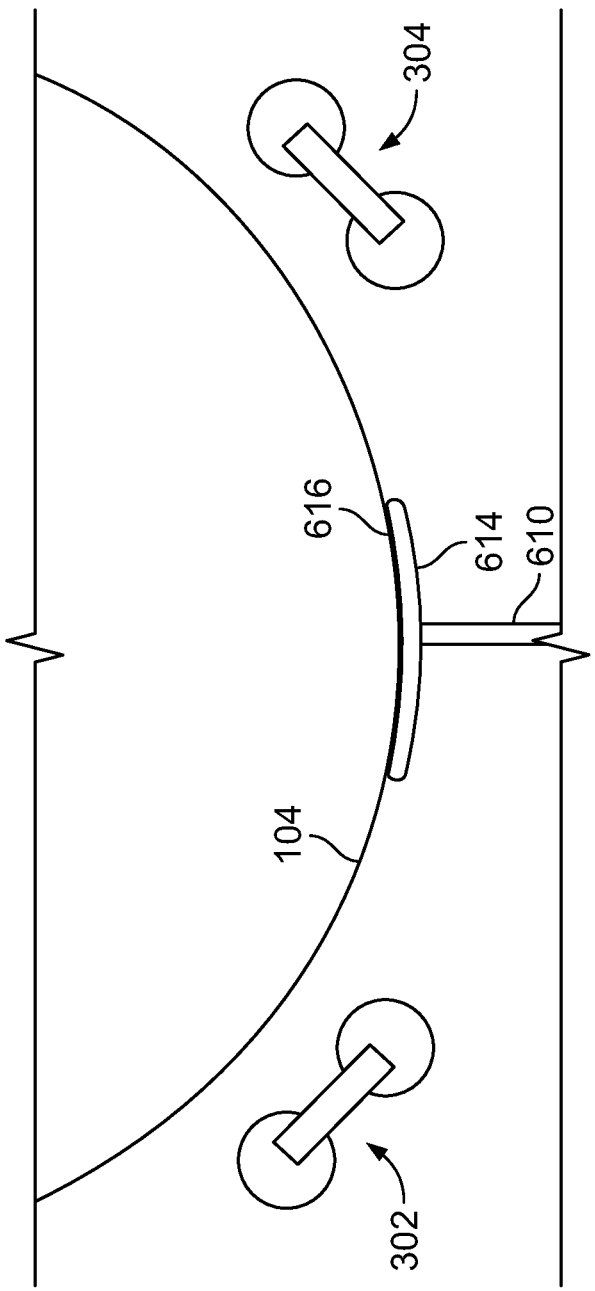
FIG. 8 illustrates an example lift unit in a raised position supporting the rotating unit.

Referring to FIG. 7, the lift unit 600 may be moved between the lowered position (e.g., illustrated in FIG. 6) and a raised position (e.g., illustrated in FIG. 8). FIG. 7 illustrates the lift unit 600 in an intermediate position that is at a height between the lowered position and the raised position. In an example, a user may desire to perform maintenance and/or inspection on one or more portions of the radiation system 200. Such maintenance and/or inspection may be facilitated by raising the rotating unit 104 such that the rotating unit 104 is no longer supported by the wheel unit 230 (e.g., the wheel mechanism 234, the second wheel mechanism 236, the third wheel mechanism 302, and the fourth wheel mechanism 304). As such, to raise the rotating unit 104, the lift unit 600 may be raised from the lowered position.

In an example, to raise the lift unit 600, the lift shaft 610 can be rotated relative to the base 602. Due to the engagement of the threading of the lift shaft 610 and the base 602, rotation of the lift shaft 610 in a direction can cause the lift shaft 610 to move upwardly (e.g., toward the rotating unit 104) in a first direction and thus cause the engagement member 614 to move into contact with the rotating unit 104.

FIG. 8 illustrates a generic representation of the second end 204 of the rotating unit 104 as viewed from the perspective indicated by lines 8-8 of FIG. 3. In an example, the lift unit 600 is illustrated in the raised position relative to the rotating unit 104. That is, in an example, the rotating unit 104 may be supported by the lift unit 600, such that the rotating unit 104 may be spaced a second distance apart from the third wheel mechanism 302, the fourth wheel mechanism 304, etc. In an example, as the lift shaft 610 continues to be rotated in the direction that causes the lift shaft 610 to move upwardly (e.g., in the first direction), the engagement member 614 can contact and engage a bottom of the rotating unit 104. For example, the engagement surface 616 of the engagement member 614 can engage the outer surface of a bottom of the rotating unit 104. Due to the force of gravity, the rotating unit 104 can rest upon the engagement surface 616, with the engagement member 614 lifting the rotating unit 104 off of the third wheel mechanism 302, the fourth wheel mechanism 304, etc. In this way, a user can access portions of the wheel unit 230 (e.g., the wheel mechanism 234, the second wheel mechanism 236, the third wheel mechanism 302, and the fourth wheel mechanism 304) to inspect and/or service and/or perform maintenance on the portions of the wheel unit 230. Moreover, in addition to inspection, servicing, and/or maintenance, the lift unit 600 can be used during shipping of the radiation system 200. For example, the lift unit 600 can be moved to the raised position such that the rotating unit 104 is supported by the lift unit 600 (e.g., and not the wheel mechanisms). In this way, during shipment of the radiation system 200, undesired effects to the wheel mechanisms are limited, such as damage that may be caused by the rotating unit 104, setting of the wheels due to supporting the weight of the rotating unit 104, etc.

It will be appreciated that FIGS. 6 to 8 illustrate a single lift unit (e.g., lift unit 600). However, in an example, the radiation system 200 may comprise one or more lift units that may be similar or identical to the lift unit 600 illustrated with respect to FIGS. 6 to 8. For example, while the lift unit 600 may be positioned adjacent to the second end 204 of the rotating unit 104, a second lift unit that is similar or identical to the lift unit 600 may be positioned adjacent to the first end 202 of the rotating unit 104. Likewise, the lift unit 600 may comprise a resilient material that can support the weight of the rotating unit 104, such as a metal material, for example.

Figure 9:
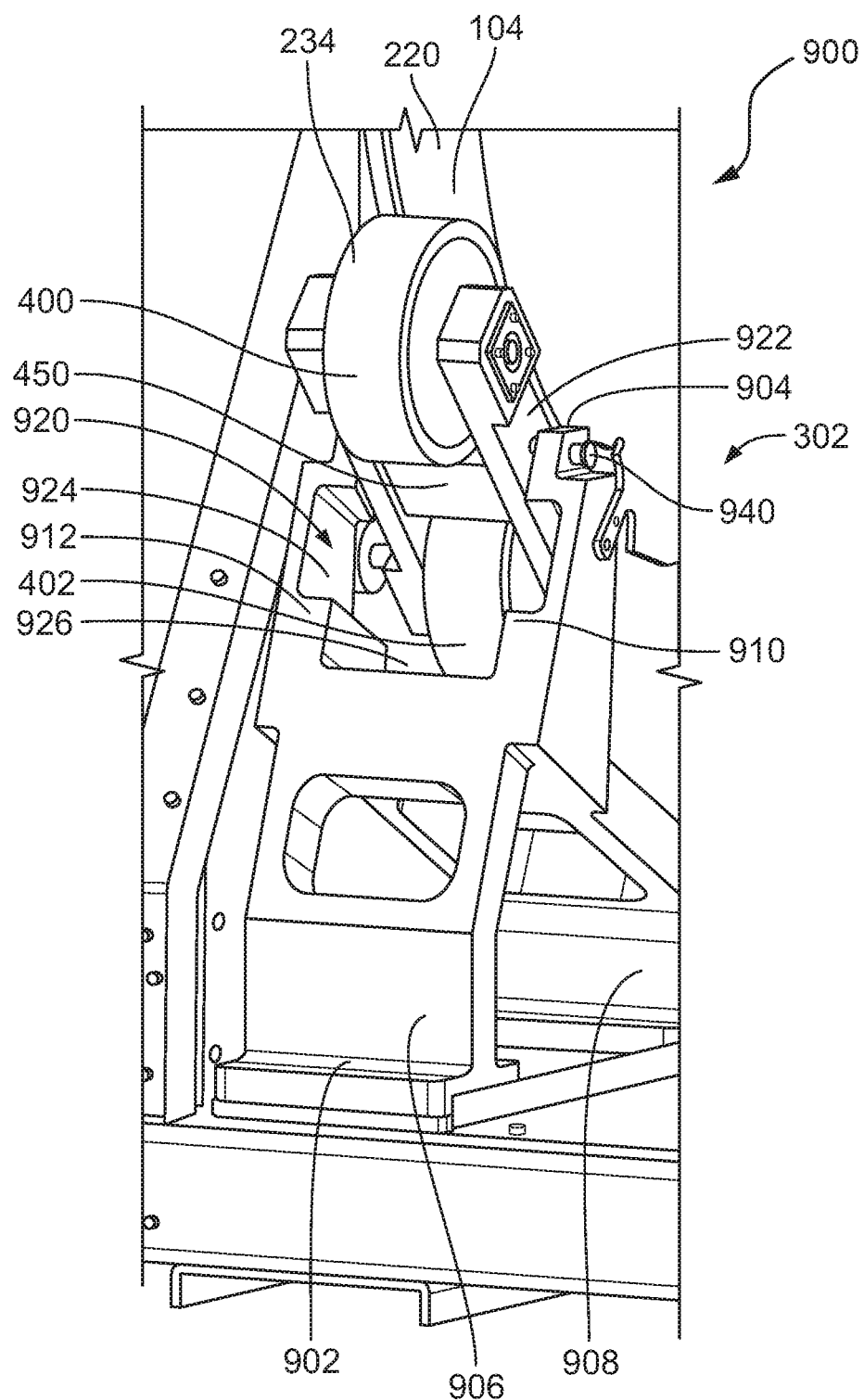
FIG. 9 illustrates an example wheel mechanism attached to an example support structure.

Referring to FIG. 9, a support structure 900 is illustrated for supporting the wheel mechanism 234. It will be appreciated that for the purposes of illustration, one support structure 900 is illustrated for supporting the wheel mechanism 234. However, in an example, the second wheel mechanism 236, the third wheel mechanism 302, and the fourth wheel mechanism 304 can similarly be supported by support structures. The support structures that support the second wheel mechanism 236, the third wheel mechanism 302, and the fourth wheel mechanism 304 can be similar and/or identical in structure, configuration, construction, etc., to the support structure 900 of FIG. 9.

The support structure 900 can extend between a first end 902 and a second end 904. The first end 902 of the support structure 900 can be attached to the stationary unit 110 while the second end 904 of the support structure 900 can support the wheel mechanism 234. In an example, the first end 902 of the support structure 900 can be attached to the stationary unit 110 in any number of ways (e.g., with mechanical fasteners, adhesives, welding, etc., so as to be substantially non-movable relative to the wheel mechanism 234.

In an example, the support structure 900 comprises one or more support legs, such as a first support leg 906 and a second support leg 908. The first support leg 906 and the second support leg 908 can be spaced apart from each other and can be attached to the stationary unit 110. In an example, the second support leg 908 can have a substantially planar top surface upon which a portion of the base 602 can rest. In this way, the second support leg 908 can support a portion of the base 602, with the base 602 resting upon the second support leg 908.

The support structure 900 comprises one or more support arms, such as a first support arm 910 and a second support arm 912. In an example, the first support arm 910 and the second support arm 912 can be attached to one or both of the first support leg 906 and the second support leg 908. In this way, the first support arm 910 and the second support arm 912 can be fixed with and/or attached to the stationary unit 110 via the first support leg 906 and the second support leg 908. In an example, the first support leg 906 and the second support leg 908 can define the first end 902 (e.g., bottom end) of the support structure 900. The first support arm 910 and the second support arm 912 can define the second end 904 (e.g., top end) of the support structure 900.

The first support arm 910 and the second support arm 912 can be spaced apart to define an opening 920 therebetween, with the opening 920 sized to receive the wheel mechanism 234. In an example, the opening 920 between the first support arm 910 and the second support arm 912 can have a non-constant size as measured from the second end 904 of the support structure 900 toward the first end 902. For example, the opening 920 may have a first opening portion 922, a second opening portion 924, and a third opening portion 926. In an example, the sizes of the first opening portion 922, the second opening portion 924, and the third opening portion 926 may not be equal. Rather, in an example, the second opening portion 924 may be greater than the first opening portion 922 and the third opening portion 926, with the second opening portion 924 located between the first opening portion 922 and the third opening portion 926.

The support structure 900 comprises an attachment structure 940 (e.g., also illustrated in FIGS. 10A, 10B and 11) that is configured to attach the wheel mechanism 234 to the support structure 900. In an example, the attachment structure 940 comprises any number of mechanical fasteners, such as screws, bolts, etc. The attachment structure 940 may be received through a support opening 950 (e.g., illustrated in FIGS. 10A and 10B) defined within the first support arm 910 and the second support arm 912. For example, the first support arm 910 and the second support arm 912 can each define one support opening 950, with the support openings 950 configured to receive the attachment structure 940. In this way, the attachment structure 940 is configured to be received through the support openings 950 of the first support arm 910 and the second support arm 912. In an example, when the attachment structure 940 is received through the support openings 950, the attachment structure 940 can extend between the first support arm 910 and the second support arm 912, while extending through the first opening portion 922 of the opening 920.

The attachment structure 940 can be placed in a locked position, such that the attachment structure 940 engages the wheel mechanism 234 and the support structure 900 such that the wheel mechanism 234 may be attached to the support structure 900. For example, the attachment structure 940 can be inserted through the support openings 950 of the first support arm 910 and the second support arm 912, and may also be inserted through the third linking opening 452 (e.g., illustrated in FIG. 5) of the third linking structure 450 of the wheel mechanism 234. In an example, the support structure 900 may be aligned with the third linking structure 450 such that the attachment structure 940 can be received through the third linking opening 452 and the support openings 950, the linking opening 424 of the first linking structure 410, and the second linking opening 430 of the second linking structure 412 when the attachment structure 940 is in the locked position.

In this way, in the locked position the attachment structure 940 can extend between the first roller 400 and the second roller 402 when the attachment structure 940 is received through the third linking opening 452. As such, the wheel mechanism 234 may be pivotable relative to the support structure 900, thus accommodating for differences in sizes (e.g., diameters) of the rotating unit 104, thermal expansion and/or contraction of the rotating unit 104, etc. For example, the wheel mechanism 234 may be pivotable about the attachment structure 940. In the locked position, the wheel mechanism 234 is attached to the support structure 900, such that the wheel mechanism 234 can support the rotating unit 104 and facilitate rotation of the rotating unit 104 relative to the stationary unit 110.

Figure 10A:
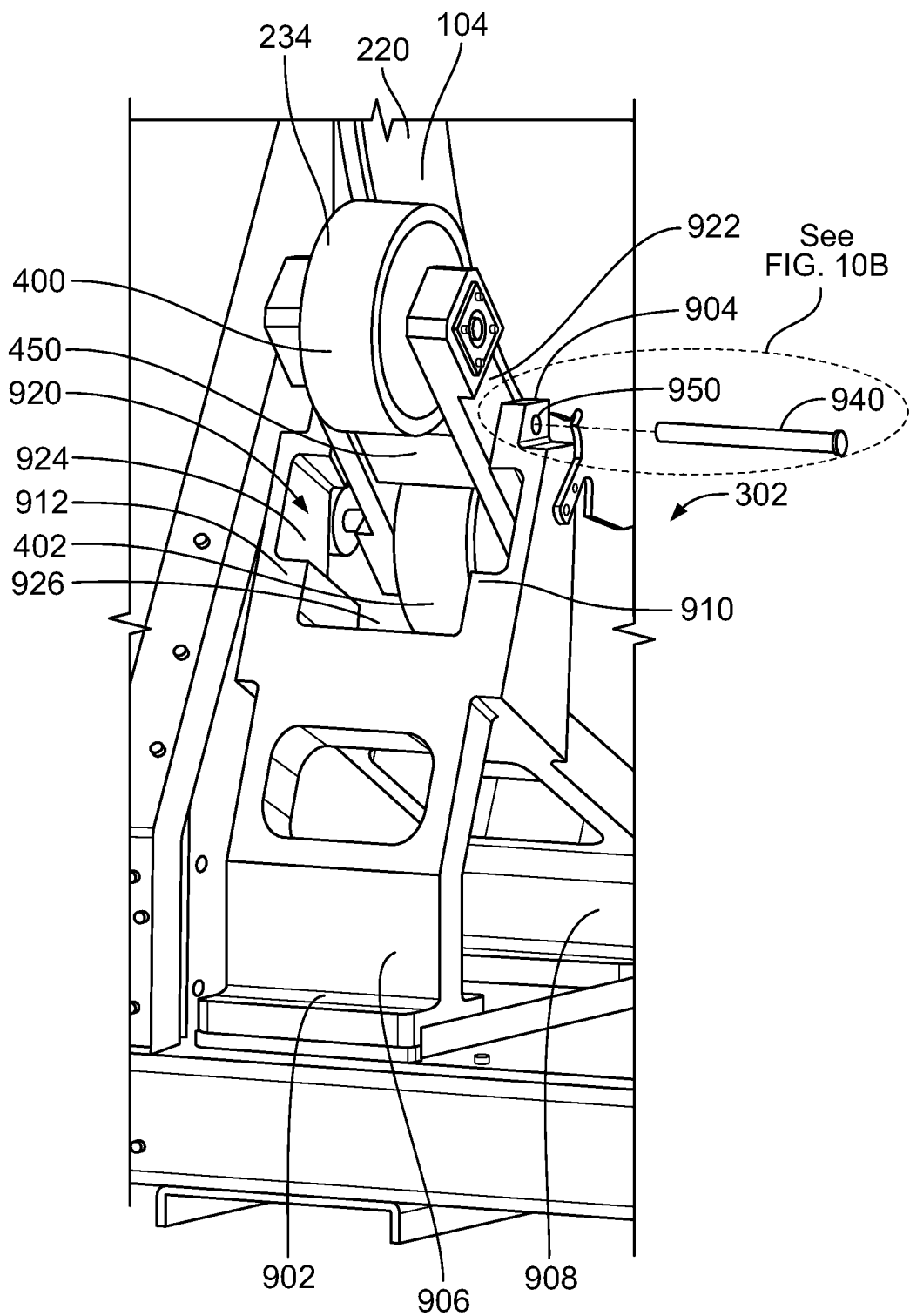
FIG. 10A illustrates an example wheel mechanism detached from an example support structure.
Figure 10B:
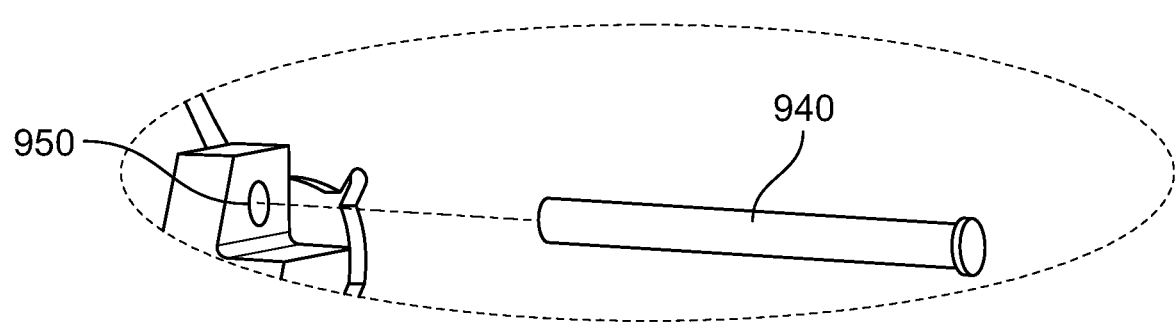
FIG. 10B illustrates an example attachment structure removed from a support opening of an example support structure.

Referring to FIGS. 10A and 10B, the attachment structure 940 is illustrated in an unlocked position. When the attachment structure 940 is in the unlocked position, the attachment structure 940 does not engage at least one of the wheel mechanism 234 or the support structure 900. For example, when the attachment structure 940 is in the unlocked position, the attachment structure is not received through the third linking opening 452 of the wheel mechanism 234 or the support openings 950 of the support structure 900. As such, the wheel mechanism 234 may be detached from the support structure 900 and may be removable from the support structure 900 through the opening 920. In an example, in the unlocked position, the attachment structure 940 may be removed from the third linking opening 452 (e.g., illustrated in FIG. 5) of the third linking structure 450 and from the support openings 950 of the first support arm 910 and the second support arm 912.

Figure 11:
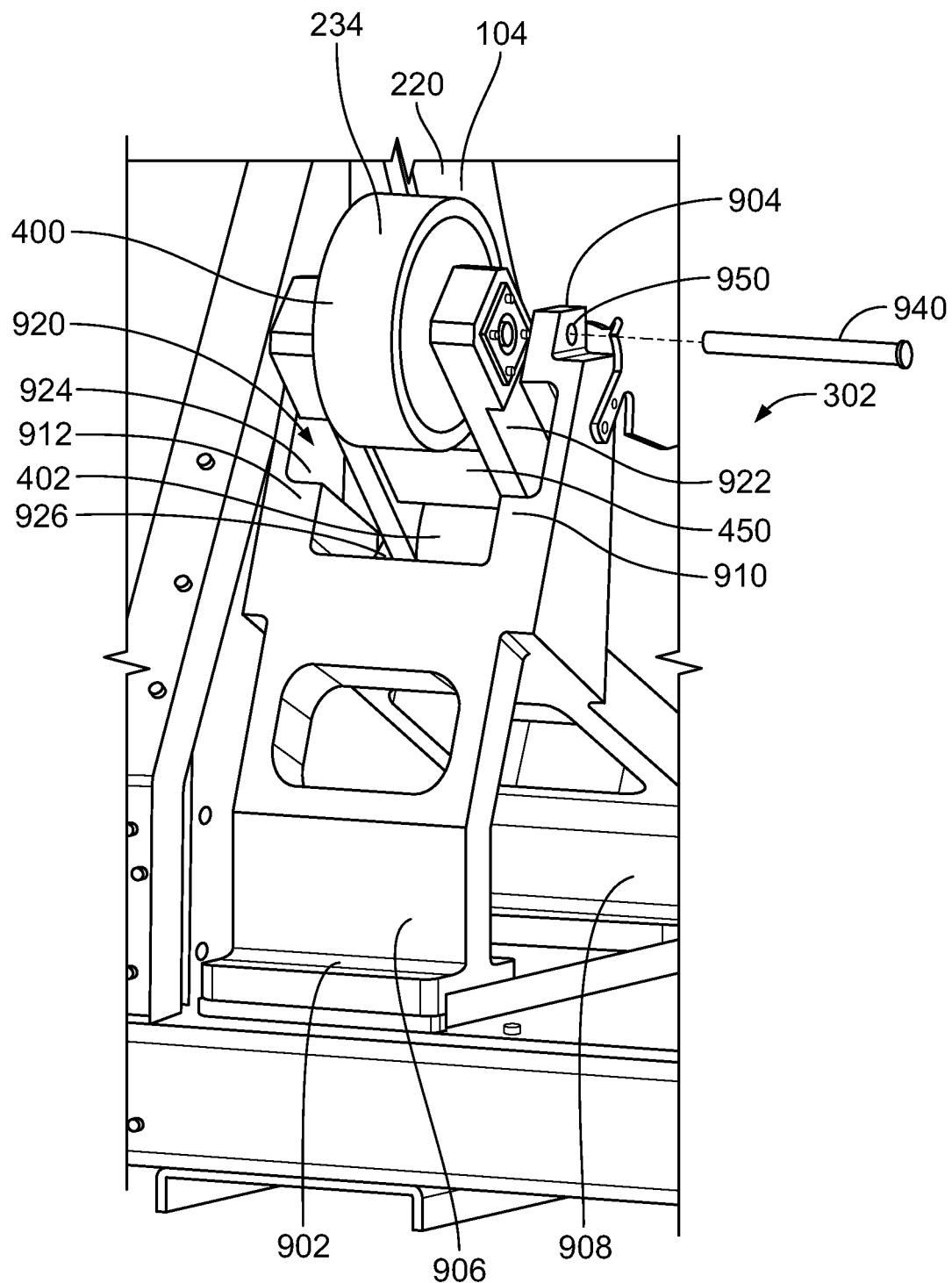
FIG. 11 illustrates an example wheel mechanism detached from an example support structure.

Referring to FIG. 11, once the attachment structure 940 has been moved to the unlocked position, the wheel mechanism 234 can be detached from the support structure 900. For example, the wheel mechanism 234 can be lowered from the first opening portion 922 of the opening 920 to the second opening portion 924. The second opening portion 924 has a larger size than the first opening portion 922, with the larger size accommodating for the size of the wheel mechanism 234. In this way, the wheel mechanism 234 can be moved through the second opening portion 924 (e.g., in a direction that is substantially perpendicular to a direction along which the attachment structure 940 extends) and removed from the support structure 900.

With the wheel mechanism 234 removed from the support structure 900, a user can perform maintenance on the wheel mechanism 234. In an example, while the attachment structure 940 is in the locked position and prior to removing the wheel mechanism 234, the lift unit 600 (e.g., illustrated in FIGS. 6 to 8) can be moved to the raised position such that the lift unit 600 can support the rotating unit 104. That is, the rotating unit 104 can rest upon and be supported by the lift unit 600, with the rotating unit 104 not supported by one or more of the wheel mechanism 234, the second wheel mechanism 236, the third wheel mechanism 302, and/or the fourth wheel mechanism 304. With the rotating unit 104 supported by the lift unit 600, the attachment structure 940 can be moved to the unlocked position (e.g., illustrated in FIGS. 10A, 10B, and 11) such that the wheel mechanism 234 can be detached from the support structure 900. It will be appreciated that the second wheel mechanism 236, the third wheel mechanism 302, and the fourth wheel mechanism 304 can be supported in a similar manner by respective support structures. Likewise, the second wheel mechanism 236, the third wheel mechanism 302, and the fourth wheel mechanism 304 can be removed from the respective support structures in a similar manner as described with respect to FIGS. 9 to 11, such as by moving an attachment structure from a locked to an unlocked position.

The wheel mechanism 234 can be re-attached to the support structure 900 by carrying out aforementioned steps in reverse. For example, the wheel mechanism 234 can first be inserted through the second opening portion 924. Next, the third linking structure 450 can be aligned with the support structure 900, such that the third linking opening 452 of the third linking structure 450 and the support openings 950 of the first support arm 910 and the second support arm 912 can be aligned. In this way, the attachment structure 940 can be passed through the third linking opening 452 and the support openings 950 so as to attach the wheel mechanism 234 to the support structure 900. When the wheel mechanism 234 is attached to the support structure 900, the wheel mechanism 234 can support the rotating unit 104.

It may be appreciated that "example" and/or "exemplary" are used herein to mean serving as an example, instance, or illustration. Any aspect, design, etc., described herein as "example" and/or "exemplary" is not necessarily to be construed as advantageous over other aspects, designs, etc. Rather, use of these terms is intended to present concepts in a concrete fashion. As used in this disclosure, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this disclosure and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure that performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A support unit for a radiation system, the support unit comprising:
    a wheel mechanism configured to at least partially support a rotating unit and facilitate rotation of the rotating unit relative to a stationary unit, the wheel mechanism comprising at least one roller that is configured to impart rotation to the rotating unit, wherein a radiation source and a detector array are mounted to the rotating unit;
    a support structure configured to support the wheel mechanism, the support structure defining an opening that is sized to receive the wheel mechanism;
    an attachment structure configured to attach the wheel mechanism to the support structure, wherein:
        when the attachment structure is in a locked position, the attachment structure engages the wheel mechanism and the support structure such that the wheel mechanism is attached to the support structure; and
        when the attachment structure is in an unlocked position, the attachment structure does not engage at least one of the wheel mechanism or the support structure such that the wheel mechanism is detached from the support structure and removable from the support structure through the opening; and
    a lift unit supported by the stationary unit and configured to engage the rotating unit, the lift unit comprising an engagement member positioned below a rounded exterior surface of the rotating unit, the engagement member comprising an engagement surface having a shape at least substantially matching a shape of the rounded exterior surface, wherein:
        when the lift unit is in a lowered position relative to the rotating unit, the rotating unit is supported by the wheel mechanism and the engagement member of the lift unit is spaced a distance apart from the rotating unit; and
        when the lift unit is in a raised position relative to the rotating unit, the rotating unit is supported from below by the engagement member of the lift unit and the rotating unit is spaced a second distance apart from the wheel mechanism.

2. The support unit of claim 1, wherein the support structure extends between a first end and a second end of the support structure, the first end of the support structure attached to the stationary unit and the second end of the support structure supporting the wheel mechanism.

3. The support unit of claim 1, wherein the at least one roller of the wheel mechanism comprises a first roller and a second roller, a linking structure attaching the first roller and the second roller.

4. The support unit of claim 3, wherein the linking structure defines a linking opening through which the attachment structure is configured to be received.

5. The support unit of claim 4, wherein the attachment structure extends between the first roller and the second roller when the attachment structure is received through the linking opening such that the wheel mechanism is pivotable relative to the support structure.

6. The support unit of claim 4, wherein the support structure defines a support opening through which the attachment structure is configured to be received, the support structure aligned with the linking structure such that the attachment structure is received through the linking opening and the support opening when the attachment structure is in the locked position.

7. The support unit of claim 6, wherein when the attachment structure is in the unlocked position, the attachment structure is not received through the linking opening and the support opening.

8. A radiation system comprising:
a stationary unit;
a rotating unit configured for rotation about an axis relative to the stationary unit, the axis lying within a plane that bisects the rotating unit, the rotating unit comprising a first rotational surface extending about the axis and a second rotational surface extending about the axis, wherein a radiation source and a detector array are mounted to the rotating unit;
a wheel mechanism set configured to at least partially support the rotating unit at the first rotational surface and facilitate rotation of the rotating unit relative to the stationary unit, the wheel mechanism set comprising:
a wheel mechanism configured to rotationally support the rotating unit at a first location of the first rotational surface, the first location lying on a first side of the plane;
a second wheel mechanism configured to rotationally support the rotating unit at a second location of the first rotational surface, the second location lying on the first side of the plane;
a second wheel mechanism set configured to at least partially support the rotating unit at the second rotational surface and facilitate rotation of the rotating unit relative to the stationary unit, the second wheel mechanism set comprising:
a third wheel mechanism configured to rotationally support the rotating unit at a third location of the second rotational surface, the third location lying on the first side of the plane; and
a fourth wheel mechanism configured to rotationally support the rotating unit at a fourth location of the second rotational surface, the fourth location lying on the first side of the plane; and
a lift unit supported by the stationary unit and configured to engage the rotating unit, the lift unit comprising an engagement member positioned below a rounded exterior surface of the rotating unit, the engagement member comprising an engagement surface having a shape at least substantially matching a shape of the rounded exterior surface, wherein:
when the lift unit is in a lowered position relative to the rotating unit, the rotating unit is supported by the wheel mechanism and the engagement member of the lift unit is spaced a distance apart from the rotating unit; and
when the lift unit is in a raised position relative to the rotating unit, the rotating unit is supported from below by the engagement member of the lift unit and the rotating unit is spaced a second distance apart from the wheel mechanism.

9. The radiation system of claim 8, wherein a wheel axis intersects the wheel mechanism and the third wheel mechanism, the wheel axis extending substantially parallel to the axis.

10. The radiation system of claim 9, wherein a second wheel axis intersects the second wheel mechanism and the fourth wheel mechanism, the second wheel axis extending substantially parallel to the axis.

11. The radiation system of claim 8, the wheel mechanism comprising a first roller and a second roller that are configured to impart rotation to the rotating unit.

12. The radiation system of claim 11, comprising a motor that is coupled to the first roller, the motor configured to impart rotation to the first roller.

13. The radiation system of claim 8, the rotating unit extending between a first end and a second end along the axis.

14. The radiation system of claim 13, the wheel mechanism comprising an axial roller that is configured to engage the first end of the rotating unit and limit movement of the rotating unit along the axis.

15. The radiation system of claim 14, the third wheel mechanism comprising a third axial roller that is configured to engage the second end of the rotating unit and limit movement of the rotating unit along the axis, the rotating unit disposed between the axial roller and the third axial roller.

16. A radiation system comprising:
a stationary unit;
a rotating unit configured for rotation about an axis relative to the stationary unit, wherein a radiation source and a detector array are mounted to the rotating unit;
a wheel mechanism configured to at least partially support the rotating unit and facilitate rotation of the rotating unit relative to the stationary unit; and
a lift unit supported by the stationary unit and configured to engage the rotating unit, the lift unit comprising an engagement member positioned below a rounded exterior surface of the rotating unit, the engagement member comprising an engagement surface having a shape at least substantially matching a shape of the rounded exterior surface, wherein:
when the lift unit is in a lowered position relative to the rotating unit, the rotating unit is supported by the wheel mechanism and the engagement member of the lift unit is spaced a distance apart from the rotating unit; and
when the lift unit is in a raised position relative to the rotating unit, the rotating unit is supported from below by the engagement member of the lift unit and the rotating unit is spaced a second distance apart from the wheel mechanism.

17. The radiation system of claim 16, comprising a base attached to the stationary unit, the base defining a base opening through which a portion of the lift unit is received, the lift unit movable relative to the base.

18. The radiation system of claim 17, wherein the lift unit extends along a direction intersecting with the axis.

\* \* \* \* \*